United States Patent
Banco

(10) Patent No.: US 10,232,075 B2
(45) Date of Patent: Mar. 19, 2019

(54) REFILL AND METHOD OF EMITTING TWO OR MORE COMPOSITIONS FROM A REFILL

(71) Applicant: S.C. Johnson & Son, Inc., Racine, WI (US)

(72) Inventor: Michael J. Banco, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 15/508,850

(22) PCT Filed: Sep. 10, 2015

(86) PCT No.: PCT/US2015/049290
§ 371 (c)(1),
(2) Date: Mar. 3, 2017

(87) PCT Pub. No.: WO2016/044043
PCT Pub. Date: Mar. 24, 2016

(65) Prior Publication Data
US 2017/0246335 A1    Aug. 31, 2017

Related U.S. Application Data

(60) Provisional application No. 62/050,251, filed on Sep. 15, 2014.

(51) Int. Cl.
*A61L 9/012*    (2006.01)
*A61L 9/12*     (2006.01)
*A01M 1/20*     (2006.01)

(52) U.S. Cl.
CPC .......... *A61L 9/125* (2013.01); *A01M 1/2044* (2013.01); *A61L 9/012* (2013.01); *A61L 9/127* (2013.01);
(Continued)

(58) Field of Classification Search
CPC ........ B65D 81/32; A01M 1/2022; A61L 9/02; A61L 9/03; A61L 9/035; A61L 9/12; F24F 3/16
(Continued)

(56) References Cited

U.S. PATENT DOCUMENTS 5,139,864 A    8/1992  Lindauer
6,968,124 B1 * 11/2005  Varanasi ............. A01M 1/2077
                                               392/392
(Continued)

FOREIGN PATENT DOCUMENTS

DE    102006060152    6/2008
GB      2395126       5/2004
(Continued)

OTHER PUBLICATIONS

International Search Report and Written Opinion issued in corresponding PCT Application No. PCT/US2015/049290, dated Dec. 7, 2015, 11 pages.

*Primary Examiner* — Viet Le
(74) *Attorney, Agent, or Firm* — Quarles & Brady LLP

(57) ABSTRACT

A refill comprises, a container having a body forming a reservoir and an opening in communication with the reservoir, a first composition disposed within the reservoir, a second composition disposed within the reservoir and substantially separated from the first composition, a single wick in contact with the first and second compositions and configured to sequentially emit the first and second compositions. A method of emitting the first and second compositions includes the steps of emitting the first composition until the first composition is substantially depleted and emitting the second composition after the first composition is substantially depleted.

15 Claims, 6 Drawing Sheets

(52) U.S. Cl.
CPC .... *A61L 2209/111* (2013.01); *A61L 2209/133* (2013.01)

(58) Field of Classification Search
USPC ...................................................... 239/34–60
See application file for complete search history.

(56) References Cited

U.S. PATENT DOCUMENTS

| | | | |
|---|---|---|---|
| 7,055,764 B1 * | 6/2006 | Martinez | A01M 1/2033 239/145 |
| 2008/0251599 A1 * | 10/2008 | Ward | A01M 1/2044 239/44 |

FOREIGN PATENT DOCUMENTS

| | | |
|---|---|---|
| WO | 2006038323 | 4/2006 |
| WO | 2009150403 | 12/2009 |

* cited by examiner

REFILL AND METHOD OF EMITTING TWO OR MORE COMPOSITIONS FROM A REFILL

BACKGROUND

1. Field of the Disclosure

The present disclosure relates generally to refills and, more particularly, to volatile material refills and methods sequentially emitting compositions from refills.

2. Description of the Background

It is known that the perception of a user of a dispensed fragrance at a constant intensity tends to decay over time. This decay in perception, which is commonly referred to as adaptation and/or habituation, reduces the enjoyment of the dispensed fragrance by the user. Adaptation and/or habituation are the reduction of physiological, psychological, or behavioral response occurring when a specific stimulus occurs repeatedly. It is generally believed that adaptation and/or habituation with respect to a fragrance can be reduced by changing the level of intensity of the dispensed fragrance or by dispensing a different fragrance. Fragrance dispensers and methods of dispensing fragrances that address the issue of adaptation and/or habituation are known in the art.

One such fragrance dispenser emits a first fragrance from a first refill for a first period of time followed by emission of a second fragrance from a second refill for a second period of time followed by emission of a third fragrance from a third refill for a third period of time. A further pattern or algorithm for dispensing fragrances includes emission of a first fragrance from a first refill in repeated short intermittent bursts during a first period of time, the emission of a second fragrance from a second refill in repeated short intermittent bursts during a second period of time, and the emission of a third fragrance from a third refill in repeated short intermittent bursts during a third period of time. In any of the above-described patterns or algorithms, one or more fans, heaters, or any suitable devices may be utilized to facilitate emission of each of the fragrances.

Another dispenser emits fragrances in an alternating sequence while the dispenser is activated. The dispenser includes, for example, first and second heaters for emitting first and second fragrances, respectively, from first and second refills, respectively. In one embodiment, the fragrances are alternatively emitted by deactivating one of the heaters at the same time the other of the heaters is activated. Alternatively, one of the heaters may be deactivated followed by a gap period and then the other of the heaters may be activated. Still further, one of the heaters may be activated before the other of the heaters is deactivated to create an overlap period. Existing devices offering solutions to adaptation and/or habituation may change dispensed fragrances or intensities thereof frequently over a period of a day or several hours, for example, every 45 minutes, thereby exposing a user to a seemingly constant change of fragrance.

Current multi-fragrancing devices require multiple refills and/or multiple actuators for emitting different fragrances. Multiple refills and/or multiple actuators increase the footprint and/or overall size of a dispenser from which the fragrances are emitted and/or increase the overall cost of the dispenser.

SUMMARY

In an illustrative embodiment, a method of emitting two or more compositions from a refill is disclosed, wherein the refill includes a container having a body forming a reservoir and an opening in communication with the reservoir, a first composition disposed within the reservoir, a second composition disposed within the reservoir and substantially separated from the first composition, and a wick in contact with each of the first and second compositions and extending out of the container. The method may comprise the steps of emitting the first composition until the first composition is substantially depleted, emitting the second composition after the first composition is substantially depleted, and activating an indicator within the second composition upon emission of the second composition.

In some embodiments, the indicator may be a dye or a colorant disposed within only the second composition. In some embodiments, activation of the indicator includes the step of transporting the dye or colorant with the second composition through the wick to change a color of the wick.

In other embodiments, the indicator may include different active materials in the first and second compositions. In still other embodiments, the indicator may include different fragrance notes within the first and second compositions.

In some embodiments, the second composition may have a greater density than the first composition. In other embodiments, the first composition may have a greater density than the first composition.

In some embodiments, the first composition is an oil-based fragrance and the second composition is a water-based fragrance.

The method may further include the step of providing a sheath fully around at least a portion of a length of the wick.

In another illustrative embodiment, a refill includes a container having a body forming a reservoir and an opening in communication with the reservoir, a first composition disposed within the reservoir, and a second composition disposed within the reservoir and substantially separated from the first composition. The first composition may have a different fragrance characteristic than the second composition. The refill may further include a single wick in contact with the first and second compositions and configured to sequentially emit the first and second compositions.

In some embodiments, the first composition may be a water-based fragrance and the second composition is an oil-based fragrance. In some embodiments, one or more fragrance components in the water-based fragrance have a C Log P of less than or equal to 2 and one or more fragrance components in the oil-based fragrance have a C Log P of greater than or equal to 3.

In some embodiments, the first composition may be emitted sequentially before the second composition and the second composition may include an indicator that alerts a user of a condition.

In some embodiments, the wick may be comprised of a single material throughout.

In some embodiments, a sheath may be disposed fully around at least a portion of a length of the wick.

BRIEF DESCRIPTION OF THE DRAWINGS

Other aspects and advantages of the present disclosure will become apparent upon consideration of the following detailed description, wherein similar structures have like or similar reference numerals.

DETAILED DESCRIPTION

The present application is directed to volatile material refills and methods of sequentially emitting two or more compositions from a refill. While the present application may be embodied in many different forms, several specific embodiments are discussed herein with the understanding that the present application is to be considered only as an exemplification of the principles of the application, and it is not intended to limit the application to the embodiments illustrated.

Figure 1:
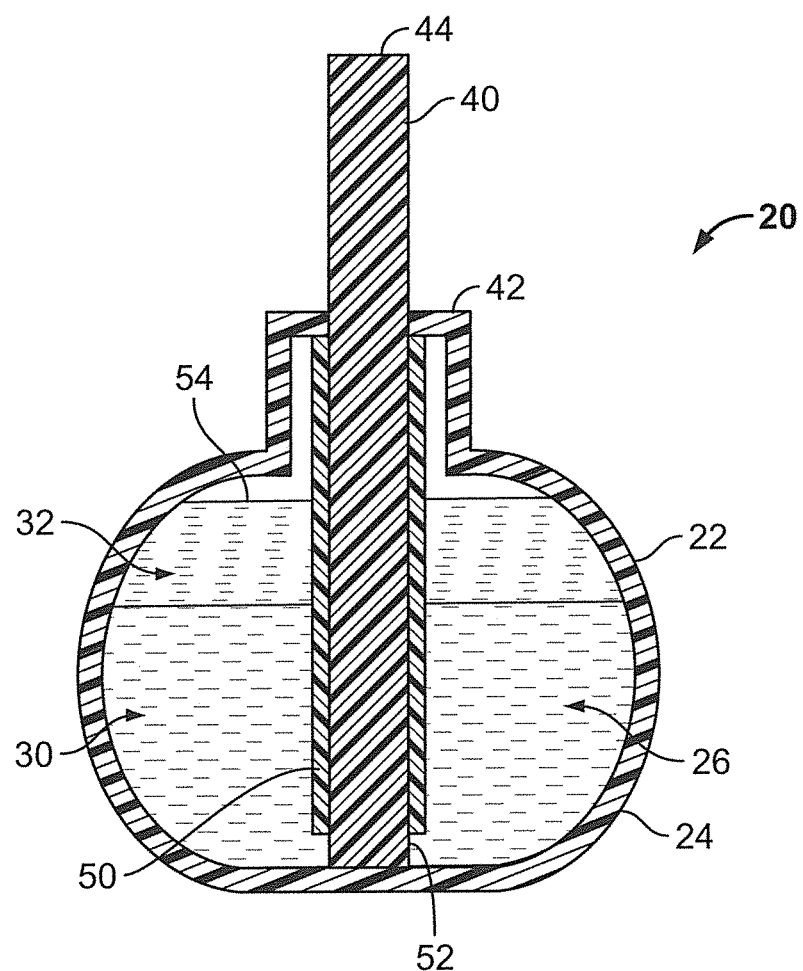
FIG. 1 is a cross-sectional view of a first embodiment of a refill including a container having a reservoir holding first and second compositions and a wick in contact with the first and second compositions and extending out of the refill.

Referring to the drawings, FIG. 1 depicts a first embodiment of a refill 20 of the present disclosure. The refill 20 may include a container 22 including a body 24 having a reservoir 26 for holding one or more liquids. The container 22 may further include a hollow neck 28 extending from the body 24 and in communication with the reservoir 26. The container 22 may be made of plastic or any other suitable material. Further, while the refill 20 is depicted as having a particular configuration, the principles of the present disclosure may be utilized in conjunction with any suitable refill.

Two or more different compositions may be held within the reservoir 26 of the container 22, as seen in FIG. 1. A first composition 30 and a second composition 32 may be layered within the reservoir 26, for example, with the first composition 30 below the second composition 32. In the embodiments disclosed herein, the first and second compositions 30, 32 may be sequentially emitted with the first composition 30 emitted first and the second composition 32 emitted second or the second composition 32 emitted first and the first composition 30 emitted second.

The first and/or second compositions 30, 32 may be any suitable liquid or liquids and one or both of the compositions 30, 32 may include one or more active ingredients. Exemplary active ingredients include, but are not limited to, one or more of a cleaner, an insecticide, an insect repellant, an insect attractant, a disinfectant, a mold or mildew inhibitor, an antimicrobial, a fragrance comprised of one or more aroma chemicals, a disinfectant, an air purifier, an aromatherapy scent, an antiseptic, an odor eliminator, a positive fragrancing active material, an air-freshener, a deodorizer, a medicinal component, an inhalant (e.g., for relieving a cough or congestion), or the like, and combinations thereof. Regardless of the specific compositions, the first and second compositions 30, 32 may be the same or different. The first and second compositions also form a two-phase liquid wherein each of the compositions forms a separate layer within the refill 20, such that the two compositions are sequentially emitted.

Figure 2:
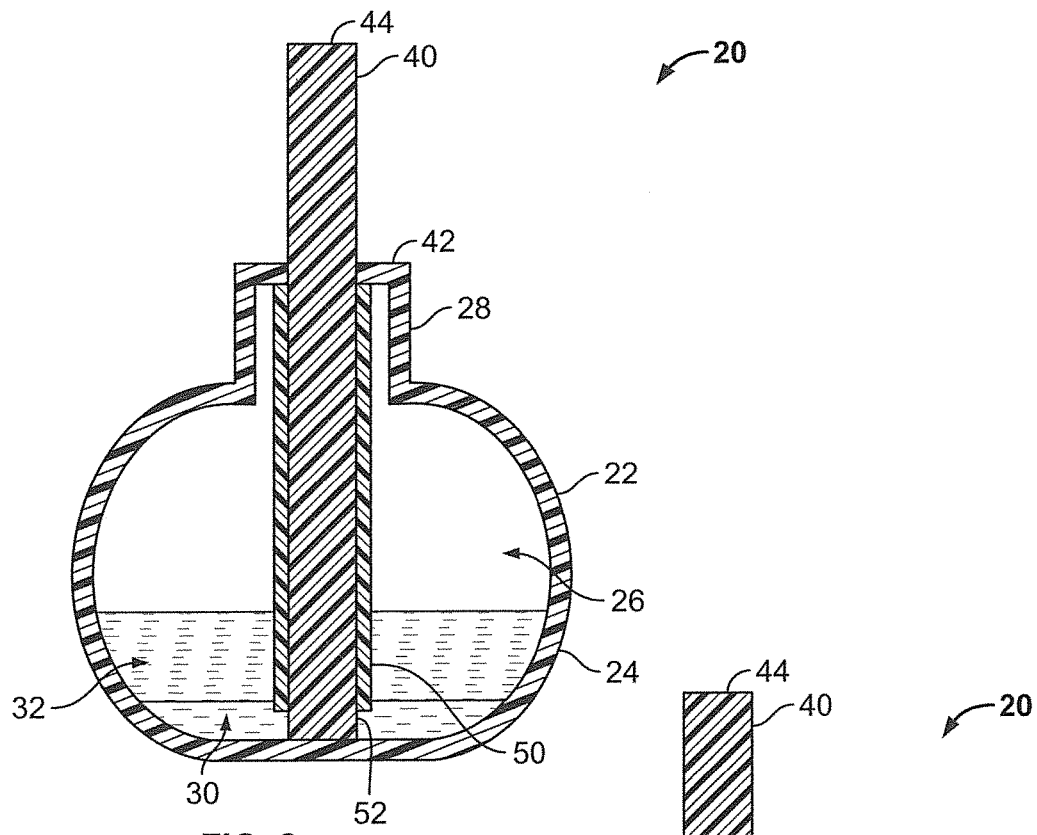
FIG. 2 is a cross-sectional view of the refill of FIG. 1, as the first composition is being depleted.
Figure 3:
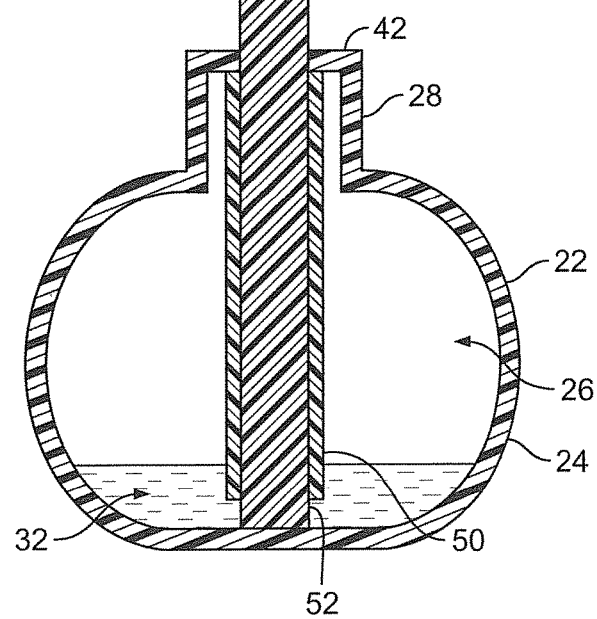
FIG. 3 is a cross-sectional view of the refill of FIG. 1, after the first composition has been fully depleted and as the second composition is being depleted.

Still referring to FIG. 1, a wick 40 is in contact with the first and second compositions 30, 32 within the reservoir 26 and extends out of the container 22 through the neck 28. A stopper or other retaining member 42 may be positioned within the neck 28 to position and retain the wick 40 within the container. The wick 40 may be made of any suitable porous material that is capable of wicking the first and second compositions 30, 32 to a top portion 44 of the wick 40 for emission into an area surrounding the refill 20. In an illustrative embodiment, the wick 40 is made of a sintered polyolefin material. A sheath 50 may be disposed about an entire perimeter of the wick 40 along a majority of a length of a portion of the wick 40 that is disposed within the reservoir 26. The sheath 50 may be formed of a plastic, metal, or any other suitable material, and may be impermeable to the first and second compositions 30, 32. In an illustrative example, as seen in FIG. 1, the sheath 50 may extend from the retaining member 42 to a point just above a bottom portion 52 of the wick 40. In other illustrative embodiments, the sheath 50 may extend to any point above an upper level 54 of the second composition 32. The bottom portion 52 of the wick 40 may be exposed so that the liquid compositions 30, 32 may move into and through the wick 40. In illustrative embodiments, the first composition 30 may be wicked through and emitted from the wick 40 first and, thereafter, the second composition 32 may be wicked through and emitted from the wick 40. While emission of the compositions 30, 32 is sequential, there may be some intermixing, and thus emission, of both of the compositions 30, 32 at the same time, for example, near the end of the first composition 30 and the beginning of the second composition 32. FIG. 2 depicts the refill 20 just prior to depletion of the first composition 30 and FIG. 3 depicts the refill after depletion of the first composition 30 and during emission of the second composition 32.

In illustrative embodiments, the first composition 30 is denser than the second composition 32 such that the first and second compositions 30, 32 form two distinct layers within the reservoir 26. In illustrative embodiments, the first composition 30 may be a water-based composition that contains one or more active ingredients, for example, a fragrance, and the second composition 32 may be an oil-based fragranced composition. In alternative embodiments, the first or second compositions 30, 32 may both be water-based or oil-based (with different densities) and/or one of the compositions 30, 32 may not include any active materials (for example, one composition may be water).

The second composition 32 may include an indicator that alerts a user that the first composition 30 has been depleted. In illustrative embodiments, the indicator may be a dye, for example, of any suitable color or colors. During emission of the first composition 30 from the refill 20, the second composition 32 is visible to a user as a distinct, colored layer of liquid material. Once the first composition 30 is substantially depleted and the second composition 32 begins to move through the wick 40, the dye is also carried through the wick 40, thereby coloring the wick 40. The change in color of the wick 40 may indicate to a user the need to replace the refill 20 or that the refill is almost empty. In illustrative embodiments, the dye may not be soluble or capable of mixing with the first composition 30. In other illustrative embodiments, both compositions 30, 32 may include a dye or colorant, wherein when the first composition is emitted, a color in the wick may appear as a first distinct color.

During a transition from the first composition 30 to the second composition 32, a color in the wick may appear as a mixture of the two colors. Further, as the first composition is completely depleted and the refill is almost empty, a color in the wick may appear as a second distinct color. In a simple example, the first color may be red, the second color may be blue, and, during the transition, the wick may be colored various shades of purple.

In alternative embodiments, the indicator may be a different active material in the second composition 32 than an active material contained in the first composition 30 and which, when activated, alerts a user to a condition within the refill. By activated, it is meant that the indicator may be sensed by a user such that the user becomes aware of a condition, for example, an empty or almost-empty refill. In an illustrative embodiment, the first composition 30 may be a water-based composition having a first active material with, for example, floral notes and the second composition 32 may be an oil-based composition having a second active material with, for example, vanilla notes. During emission of the first composition 30 from the refill 20, the user may smell a distinct floral fragrance. Once the first composition 30 is substantially depleted and the second composition 32 begins to move through the wick 40, the indicator (i.e., a different odor) is activated, and the user may smell a distinct vanilla fragrance. The change in smell or odor is an indicator that the first composition 30 has been substantially depleted and the refill 20 needs to be replaced. While one specific example is disclosed, any number of different smells or odors may be utilized, as long as the difference in the active materials is enough to alert the user to a change in composition.

In still alternative embodiments, the indicator may be the same active material at different intensity levels. The first and second compositions 30, 32 may be water and oil-based compositions, respectively, with the same or similar active materials with one of the first or second compositions 30, 32 having the active material(s) at a greater intensity level or strength. In an illustrative embodiment, the intensity level of the active material(s) in the second composition 32 may be greater than the intensity level of the active material(s) in the first composition 30. During emission of the first composition 30 from the refill 20, the user would sense the active material(s) at a normal level. Once the first composition 30 is substantially depleted and the second composition 32 begins to move through the wick 40, the indicator (i.e., a greater strength of an active material) may be activated and the active material(s) may be stronger such that the user senses a change in the level of the active material(s), thereby alerting the user to replace the refill 20 and also allowing the user to again sense a fragrance to which the user may have become habituated.

In other illustrative embodiments, the indicator may be both a dye and a different active material or intensity level in the first and second compositions 30, 32.

Figure 4:
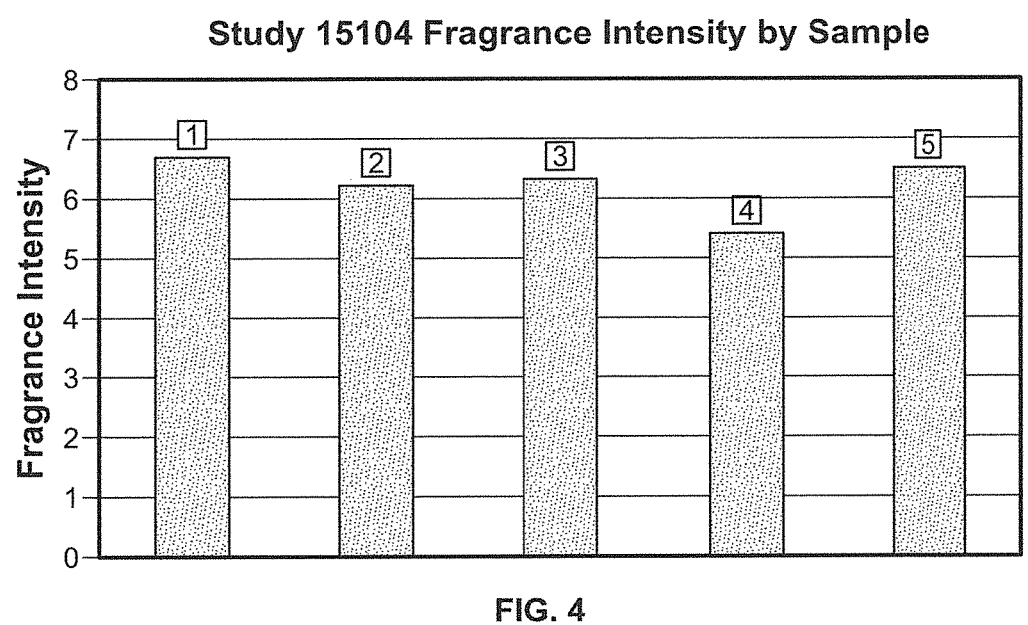
FIG. 4 is a graph depicting perceived fragrance intensity for various refills having water-based and/or oil-based fragrances.

FIG. 4 depicts perceived fragrance intensities for various refills in a trained sensory panel. Each of the individuals on the trained sensory panel was asked to rate perceived fragrance intensities on a scale of 0 to 15. In FIG. 4, Sample 1 is an oil-based fragrance delivered through an untreated wick, Sample 2 is a water-based fragrance delivered first from a two-phase liquid, where an oil-based fragrance was the top layer, Sample 3 is a water-based fragrance delivered second from a 2-phase system that included an oil-based fragrance as the top layer, Sample 4 is a water-based fragrance delivered through a sintered polyolefin wick that has been treated with a hydrophilic surfactant prior to sintering, and Sample 5 is an oil-based fragrance delivered through a wick that has been treated with a hydrophilic surfactant prior to sintering.

Samples 4 and 5 show a difference in perceived intensities for a water-based fragrance (Sample 4) and an oil-based fragrance (Sample 5) having the same fragrance notes and delivered from the same type of wick. Samples 2 and 3 show that the perceived intensities for sequential oil and water-based fragrances are higher than a perceived intensity for a water-based fragrance alone (Sample 4), but lower than a perceived intensity for an oil-based fragrance alone (Sample 1).

Figure 5:
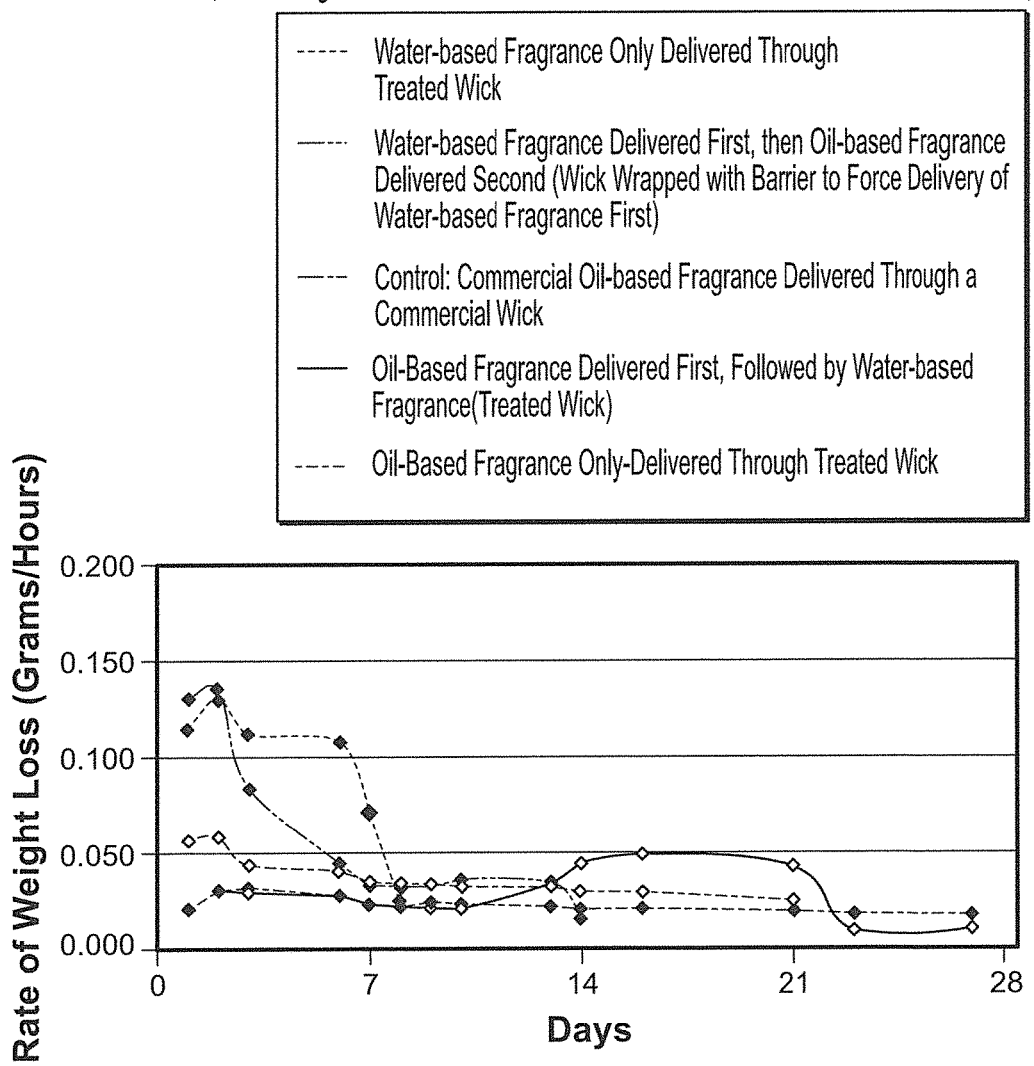
FIG. 5 is a graph depicting a rate of weight loss (in grams per hour) versus time for various compositions.

A graph depicting a rate of weight loss (in grams per hour) versus time is depicted in FIG. 5. The graph depicts weight loss for (A) a water-based fragrance, (B) a first composition 30 that is a water-based fragrance, followed by a second composition 32 that is an oil-based fragrance, wherein the wick 40 was wrapped with a barrier layer 50 (see FIGS. 1-3) to force the compositions through the bottom portion 52 of the wick 40, (C) an oil-based fragrance delivered through an unmodified wick 40, (D) a first composition 32 that is an oil-based fragrance, followed by a second composition 30 that is a water-based fragrance, and (E) an oil-based fragrance delivered through a wick 40 that has been treated to make it hydrophilic, as described above.

The first and second compositions are delivered in sequence or in sequential order. Sequential order should not be constrained to mean that there is no mixing of the two phases (first and second compositions), but rather, sequential order means that over the life of the refill, the liquid emitted from the wick varies from being substantially composed of one phase/composition at the beginning to substantially composed of another phase/composition at the end. Curve (B) depicts the delivery of mostly the water-based fragrance at first, which transitions to a delivery of mostly the oil-based fragrance near the end of the life of the liquid in the reservoir. Curve (D) depicts an upturn in the delivery rate at the end of the life of the liquid in the refill, which is caused by emitting mostly an oil-based fragrance followed by mostly a water-based fragrance. This upturn or increase in delivery provides an increase in noticeability of the fragrance (especially if different fragrances are used).

During the testing of FIG. 5, it was observed that water-based compositions move through wicks at a higher rate than oil-based compositions, but the wick will preferentially wick oil-based compositions before water-based compositions. The result is that, if an oil-based composition is to be emitted first, followed by a water-based composition, a barrier layer around the wick is not necessary. Still further, (B) and (D) include the same two compositions with reversed order of emission.

Figure 6:
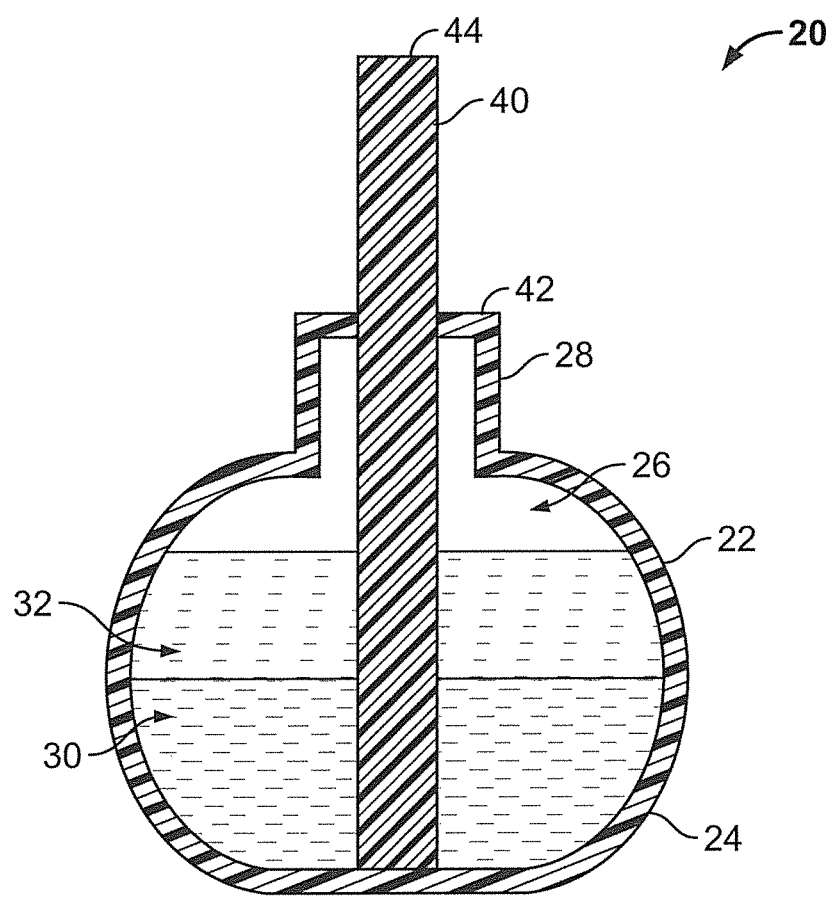
FIG. 6 is a cross-sectional view of a second embodiment of a refill including a container having a reservoir holding first and second compositions and a wick in contact with the first and second compositions and extending out of the refill.
Figure 7:
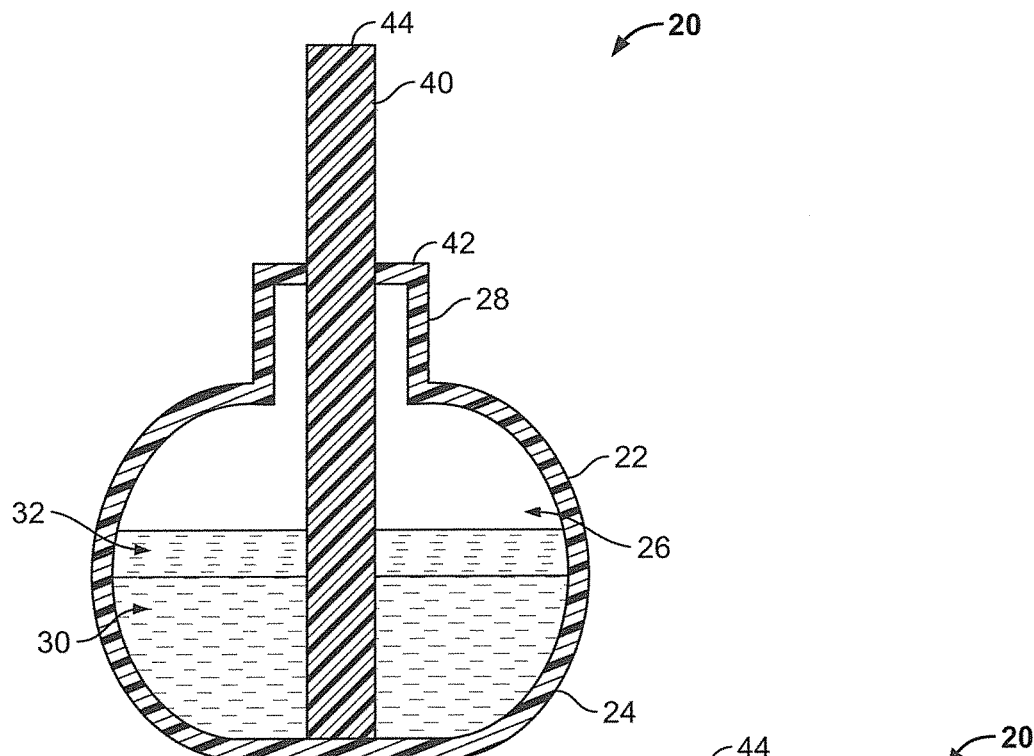
FIG. 7 is a cross-sectional view of the refill of FIG. 8, as the second composition is being depleted.
Figure 8:
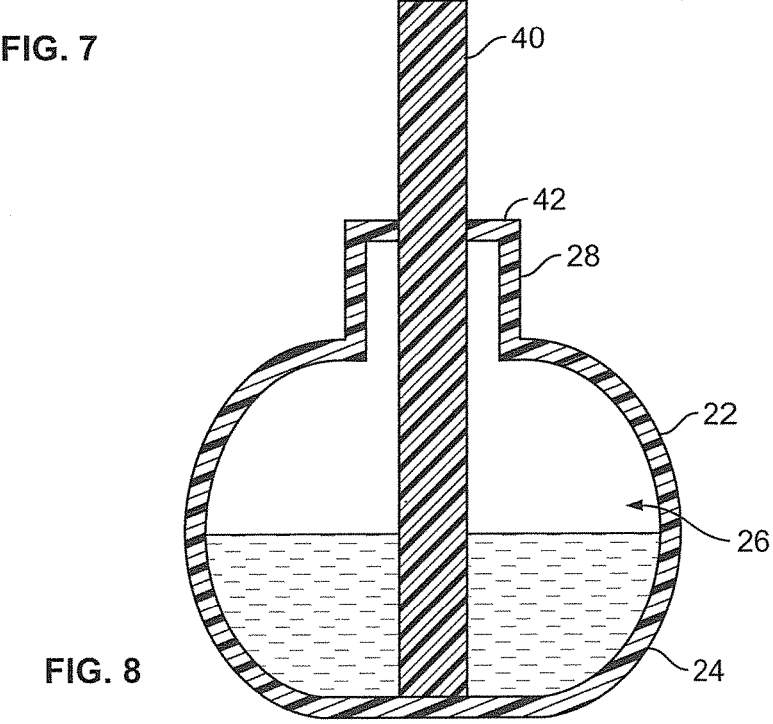
FIG. 8 is a cross-sectional view of the refill of FIG. 8, after the second composition has been fully depleted and as the second composition is being depleted.

Based on the results, as seen in FIG. 5, a second embodiment of a refill 20 was developed, as depicted in FIG. 6. The refill 20 of FIG. 6 is similar to the refill of FIGS. 1-3, except that a sheath is not disposed over the wick 40. In illustrative embodiments, the first composition 30 is a water-based fragrance and the second composition 32 is an oil-based fragrance. As seen in FIGS. 7 and 8 and noted above, the wick 40 has an affinity for the second, oil-based composition 32 and, therefore, absorbs and emits the second composition 32 first (FIG. 7). Once the second composition 32 has been substantially depleted, as seen in FIG. 8, the first composition 30 is absorbed and emitted by the wick 40.

Any of the indicators, as described above with respect to the first embodiment and FIGS. 1-3, may be utilized with the third embodiment. The indicators may be implemented and may function in the same manner as described above.

It may be important in determining fragrances or aroma chemicals for each of the compositions to be used in the refills disclosed herein, to consider fragrances for each phase or composition that stay in that phase and do not migrate to other phase(s). While perfect containment of fragrances within their phases may not be possible, selection of fragrances may be made that may bias a fragrance to one phase or another. In an illustrative embodiment, all of the fragrance components may be chosen for the water-based phase with a C Log P of 2 or less such that the fragrance components have a great affinity for the water phase. Likewise, all of the fragrance components may be chosen for the oil-based phase with a C Log P of 3 or more such that the fragrance components have a greater affinity for the oil phase.

While the illustrative embodiments described in detail herein include only two compositions, the principles of the present application may be applied to any number of the same and/or different compositions. If the compositions are to be emitted in a sequential order, the compositions may have different densities such that each individual composition will be substantially emitted before the next composition begins. In an illustrative embodiment in which more than two compositions are utilized, the phases could include a water phase, a non-polar solvent phase, and a thickened liquid or gel phase.

Any of the refills, compositions, methods, and/or indicators described in detail herein may be utilized within any passive or active dispenser or alone. Exemplary active dispensers in which the refills, compositions, and/or indicators may be utilized include, but are not limited to, those including one or more of a fan, a heater, a piezoelectric actuator, or any other suitable actuator.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present disclosure provides refills containing multiple compositions for sequential emission, which may increase the noticeably of one or more fragrances emitted from the refills. The present disclosure also provides refills and method for indicating a condition within the refill, for example, that a composition has been substantially depleted from a refill.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

I claim:

1. A method of emitting two or more compositions from a refill, the refill including a container having a body forming a reservoir and an opening in communication with the reservoir, a first composition disposed within the reservoir, a second composition disposed within the reservoir and substantially separated from the first composition, a wick defining an outer sidewall, a portion of the outer sidewall being in contact with the first composition prior to emission of either the first or second compositions, the wick extending out of the container, and a sheath surrounding a portion of the wick, a bottom edge of the sheath being spaced from a bottom edge of the wick to expose a portion of the outer sidewall of the wick, the method comprising the steps of:
    emitting the first composition until the first composition is substantially depleted, wherein the first composition has a first fragrance intensity;
    emitting the second composition after the first composition is substantially depleted, wherein the second composition has a second fragrance intensity; and
    wherein the second fragrance intensity is greater than the first fragrance intensity, thereby acting as an indicator to indicate that emission of the second composition has commenced.

2. The method of claim 1, wherein the indicator further includes a dye or colorant disposed within only the second composition.

3. The method of claim 2, wherein activation of the indicator includes the step of transporting the dye or colorant with the second composition through the wick to change a color of the wick.

4. The method of claim 1, wherein the refill includes different active materials in the first and second compositions.

5. The method of claim 1, wherein the refill includes different fragrance notes within the first and second compositions.

6. The method of claim 1, wherein the first composition has a greater density than the second composition.

7. The method of claim 1, wherein the second composition is an oil-based fragrance and the first composition is a water-based fragrance.

8. The method of claim 1, further including the step of providing the sheath fully around at least a portion of the wick.

9. The method of claim 1, wherein a lowermost end of the sheath is disposed below the second composition.

10. The method of claim 1, wherein one or more first fragrance components in the first composition have a c Log P of less than or equal to 2 and one or more second fragrance components in the second composition have a c Log P of greater than or equal to 3.

11. A refill, comprising:
    a container having a body forming a reservoir and an opening in communication with the reservoir;
    a first composition disposed within the reservoir, the first composition being a water-based composition;
    a second composition disposed within the reservoir and substantially separated from the first composition, the second composition comprising an oil-based composition, wherein the first composition has a first fragrance intensity and the second composition has a second fragrance intensity, the second fragrance intensity being greater than the first fragrance intensity;
    a single wick having an upper portion, a medial portion, and a lower portion, an outer wall of the lower portion being in contact with the first composition prior to emission of either the first or second compositions and configured to sequentially emit the first and second compositions; and a sheath surrounding the medial portion of the wick and only a portion of the lower portion of the wick.

12. The refill of claim 11, wherein one or more fragrance components in the water-based fragrance have a c Log P of less than or equal to 2 and one or more fragrance components in the oil-based fragrance have a c Log P of greater than or equal to 3.

13. The refill of claim 11, wherein the first composition is emitted sequentially before the second composition and the second composition includes an indicator that alerts a user of a condition.

14. The refill of claim 11, wherein the wick is comprised of a single material throughout.

15. The refill of claim 11, wherein a lowermost end of the sheath is disposed below the second composition.

* * * * *